United States Patent
Ishida et al.

(10) Patent No.: US 7,361,637 B2
(45) Date of Patent: Apr. 22, 2008

(54) HYPOTENSORS

(75) Inventors: Yuichi Ishida, Washimiya-machi (JP); Fumiaki Suzuki, Gifu (JP); Kazuo Murakami, Tsukuba (JP)

(73) Assignee: Protein Express Co., Ltd., Chiba (JP)

( * ) Notice: Subject to any disclaimer, the term of this patent is extended or adjusted under 35 U.S.C. 154(b) by 0 days.

(21) Appl. No.: 11/096,661

(22) Filed: Apr. 1, 2005

(65) Prior Publication Data

US 2005/0203021 A1 Sep. 15, 2005

Related U.S. Application Data

(62) Division of application No. 10/257,050, filed as application No. PCT/JP01/03034 on Apr. 9, 2001, now Pat. No. 6,900,020.

(30) Foreign Application Priority Data

Apr. 10, 2000 (JP) .............................. 2000-108670

(51) Int. Cl.
*A61K 38/00* (2006.01)
(52) U.S. Cl. ...................... 514/12; 530/300; 424/185.1
(58) Field of Classification Search ...................... None
See application file for complete search history.

(56) References Cited

U.S. PATENT DOCUMENTS 5,945,512 A 8/1999 Murakami et al. ....... 530/387.1

FOREIGN PATENT DOCUMENTS

JP 10-279600 7/2000

OTHER PUBLICATIONS

Suzuki, F. et al., Biosci. Biotechnol. Biochem. 63(3): 550-554 Mar. 1999, "Non-proteolytic activation of human prorenin by anti-prorenin prosegment (pf#1: 1P-15P) Antiserum".*
International Search Report dated Jul. 3, 2001.
Dubin et al., "Synthetic Peptide Inhibitors of Prorenin Activation," *Symposium of rennin inhibitors: Present and future held at the 12th scientific meeting of the International Society of Hypertension*, Osaka, Japan, May 28, 1988, J. Hypertens., vol. 7, suppl.2, pp. S71-S74 (1989).
Suzuki, F. et al., *Journal of Biological Chemistry*, vol. 278, No. 25, pp. 22217-22222 (2003).
Office Action issued by Canadian Patent Office dated Jul. 4, 2006 in counterpart Canadian Patent Application No. 2,404,644.
Cohen et al., "New monoclonal antibodies directed against the propart segment of human prorenin as a tool for the exploration of prorenin conformation," Journal of Immunological Methods, No. 184, 1995 (pp. 91-100).

* cited by examiner

*Primary Examiner*—Robert Mondesi
*Assistant Examiner*—Anand Desai
(74) *Attorney, Agent, or Firm*—Kilyk & Bowersox, P.L.L.C.

(57) ABSTRACT

There are provided a method for selection of a substance which is capable of controlling activation of prorenin where an adjusting ability of the activation of prorenin by protein-protein interaction in a profragment region of prorenin as indicator is used; a prorenin activation controlling substance having a function of controlling the activation of prorenin based on protein-protein interaction by a profragment region of prorenin; and hypotensor, organ hypertrophy suppressor and arterial thickening suppressor containing the prorenin activation controlling substance as an effective ingredient.

5 Claims, No Drawings

HYPOTENSORS

The present application is a divisional application of U.S. patent application Ser. No. 10/257,050, filed Dec. 30, 2002, now U.S. Pat. No. 6,900,020 B2, which is a National Stage entry of International Application No. PCT/JP01/03034 filed Apr. 9, 2001.

TECHNICAL FIELD

The present invention relates to hypotensors, organ hypertrophy suppressors and arterial thickening suppressors and also to a method for selecting the same.

BACKGROUND ART

It has been already known that a renin-angiotensin-aldosterone system participates in a rise of blood pressure (*Tokyo Joshi Idai Zasshi*, 60(4): 342-350, 1999). Actually, angiotensinogen secreted from liver is converted to angiotensin I (hereinafter, referred to as AI) by the action of renin derived from kidney and is further converted to angiotensin II (hereinafter, referred to as AII) by the action of angiotensin converting enzyme (ACE). AII directly acts on blood vessel to cause vasoconstriction and also acts on adrenal cortex to promote biosynthesis and secretion of aldosterone and to cause retention of Na and water whereupon hypertension is resulted.

Therefore, as a therapeutic method for hypertension, pharmaceutical agents acting on a renin-angiotensin system have been positioned as hypotensors of the newest type at present and ACE inhibitors have been practically used. At the same time, renin inhibitors have been studied as hypotensors but, due to their side effects, their development has been given up. ACE inhibitors are specific inhibitors for angiotensin converting enzyme and captopril (generic name) is well known. However, ACE inhibitors have side effects such as dry cough and do not exhibit a clinical efficacy to the extent of an inhibitory effect on the enzymatic activity in vitro and, therefore, a combination therapy with a renin-angiotensin system inhibitor having different action mechanism has been attempted. Accordingly, there has been a strong demand for highly effective hypotensors, blood vessel thickening suppressors and organ hypertrophy suppressors which are other than the hypotensors having been reported or used already.

Renin is biosynthesized mostly in kidney as pre-prorenin comprising 406 amino acids that is a precursor thereof whose 23 amino acids at N-terminal are cleaved to give prorenin and then 43 amino acids are further cleaved from N-terminal to give renin comprising 340 amino acids. Renin is a proteinase by which angiotensinogen is specifically hydrolyzed to produce AI. However, prorenin which is a precursor of renin does not usually exhibit such an enzymatic activity. Therefore, although the amount of prorenin existing in blood is about ten-fold of that of renin, it has been believed that the active substance in a renin-angiotensin system is renin or renin that is produced by hydrolysis of prorenin.

The present inventors previously found that, when prorenin which is an inactive renin precursor forms an immune complex in vitro as it combines with an antibody which specifically recognizes a fragment of 43 amino acid (hereinafter, referred to as "profragment" or "pf") at N-terminal which is cleaved upon at the time of production of renin from prorenin, a protein function or, in other words, an enzymatic activity (renin activity) is expressed in a non-enzymatic manner under a physiological condition without alterarion in the primary structure (Japanese Patent Laid-Open No. H10-279,600 and U.S. Pat. No. 5,945,512), using an anti-human prorenin pf antibody. With regard to a means for activation of prorenin, there have been known methods of conversion to renin using protease, a method where activation is carried out without alterarion in the primary structure under an acidic condition and a low-temperature (*Nature*, 288, 702-705, 1980), (*J. Biol. Chem.*, 262, 2472-2477, 1987), (*Clin. Chem.*, 37, 1811-1819, 1991), (*J. Biol. Chem.*, 267, 11753-11759, 1992), and a method where a low-molecular renin inhibitor is combined to an enzymatically active portion buried in the deep grooves of the three-dimensional structure of prorenin (*J. Bid. Chem.*, 267, 22837-22842, 1992) to convert into an open type, etc. However, mechanism for activation of prorenin in vivo and its function have still been ambiguous.

SUMMARY OF THE INVENTION

Taking the above-mentioned circumstances into consideration, the present inventors have carried out an investigation and found that, when an anti-pf antibody which is able to activate prorenin or a partial peptide derived from prorenin profragment which is an antigen for the said antibody is administered to a pathological animal model of hypertension, there are achieved hypotensive action, organ hypertrophy suppressing action and arterial thickening suppressing action. Thus, it has been found that, when a protein-protein interaction in a profragment region of prorenin is inhibited, activation of prorenin is suppressed in vivo and thereby it has been firstly proved that activation of prorenin takes place in vivo. On the basis of such a finding, it has been found that, when a substance that inhibits the activation of prorenin in vivo is used, provided are hypotensors, organ hypertrophy suppressors and arterial thickening suppressors and also a method for selection thereof whereupon the present invention has been achieved.

Thus, embodiments of the present invention are as follows.

1) A method for selection of a substance capable of controlling activation of prorenin in which the method is carried out using, as an indicator, an adjusting ability of the activation of prorenin which occurs by protein-protein interaction in the profragment region of prorenin without alteration in a primary structure;

2) A method for selection of a substance capable of controlling activation of prorenin in which the method is carried out using, as an indicator, an adjusting ability of the activation of prorenin by an antibody against the profragment region of prorenin;

3) The method for selection according to the above 1) or 2), wherein the substance to be selected is a substance which is designed on the basis of information of at least three amino acid sequences of the amino acid sequence in the profragment region of prorenin;

4) The method for selection according to the above 1) or 2), wherein the substance to be selected is a substance which is designed on the basis of information of at least three amino acid sequences in from the first to the 19th or from 27th to the 41st amino acid sequence from N-terminal of the amino acid sequence in the profragment region of prorenin;

5) The method for selection according to the above 1) or 2), wherein the substance to be selected is a substance which is designed on the basis of information of at least three amino acid sequences in from the 5th to the 19th amino acid sequence from N-terminal of the amino acid sequence in the profragment region of prorenin;

6) The method for selection according to any of the above 3) to 5), wherein the substance to be selected is a peptide;

7) The method for the selection according to any of the above 3) to 5), wherein the substance to be selected is a low-molecular compound;

8) The method for selection according to any of the above 1) to 7), wherein the prorenin is human prorenin;

9) The method for selection according to any of the above 1) to 7), wherein the prorenin is rat prorenin;

10) A prorenin activation controlling substance having a function of controlling activation of prorenin which occurs by protein-protein interaction in the profragment region of prorenin without alteration in a primary structure;

11) a function of controlling activation of prorenin which occurs by protein-protein interaction in the profragment region of prorenin without alteration in a primary structure, wherein the substance is selected by any of the methods mentioned in the above 1) to 9);

12) A prorenin activation controlling substance having a function of inhibiting the activation of prorenin without a primary structural change occurred by a protein-protein interaction in the profragment region of prorenin;

13) A prorenin activation controlling substance having a function of inhibiting activation of prorenin which occurs by protein-protein interaction in the profragment region of prorenin without alteration in a primary structure and retaining no renin-inhibiting activity;

14) A prorenin activation controlling substance having a function of inhibiting activation of prorenin which occurs by protein-protein interaction in the profragment region of prorenin without alteration in a primary structure, wherein the substance is selected by any of the methods mentioned in the above 1) to 9);

15) A prorenin activation controlling substance having a function of inhibiting activation of prorenin which occurs by protein-protein interaction in the profragment region of prorenin without alteration in a primary structure and retaining no renin-inhibiting activity, which is selected by any of the methods mentioned in the above 1) to 9);

16) A prorenin activation controlling substance comprising a peptide having a partial sequence selected from amino acid sequence of profragment region of prorenin or an equivalent peptide thereto and having a function of inhibiting activation of prorenin which occurs by protein-protein interaction in the profragment region of prorenin without alteration in a primary structure;

17) A prorenin activation controlling substance comprising a peptide having a continued 3 to 10 partial sequence selected from amino acid sequence of profragment region of prorenin and having a function of inhibiting activation of prorenin which occurs by protein-protein interaction in the profragment region of prorenin without alteration in a primary structure;

18) A prorenin activation controlling substance comprising a peptide having a continued 3 to 8 partial sequence selected from amino acid sequence of profragment region of prorenin and having a function of inhibiting activation of prorenin which occurs by protein-protein interaction in the profragment region of prorenin without alteration in a primary structure;

19) A prorenin activation controlling substance comprising a peptide having a continued 3 to 6 partial sequence selected from amino acid sequence of profragment region of prorenin and having a function of inhibiting activation of prorenin which occurs by protein-protein interaction in the profragment region of prorenin without alteration in a primary structure;

20) A prorenin activation controlling substance comprising a peptide selected from the peptide mentioned in SEQ ID NO: 7 to NO: 14 of the Sequence Listing and having a function of inhibiting activation of prorenin which occurs by protein-protein interaction in the profragment region of prorenin without alteration in a primary structure;

21) A prorenin activation controlling substance comprising a peptide selected from the peptide mentioned in SEQ ID NO: 3, NO: 4 and from NO: 15 to NO: 20 of the Sequence Listing and having a function of inhibiting activation of prorenin which occurs by protein-protein interaction in the profragment region of prorenin without alteration in a primary structure;

22) A prorenin activation controlling substance having a function of inhibiting activation of prorenin which occurs by protein-protein interaction in the profragment region of prorenin without alteration in a primary structure, wherein the substance is a low-molecular compound designed from the information of amino acid sequence of profragment region of prorenin;

23) The prorenin activation controlling substance according to any of the above 16) to 22), wherein the substance has a function of inhibiting activation of prorenin which occurs by protein-protein interaction in the profragment region of prorenin without alteration in a primary structure and retains no renin-inhibiting activity;

24) The prorenin activation controlling substance according to any of the above 12) to 23), wherein an effect of inhibiting activation of prorenin is caused by an antagonistic action against the protein-protein interaction in the profragment region of prorenin;

25) A prorenin activation controlling substance which is characterized in that activation of prorenin is inhibited in vivo by removal of prorenin based on an antigen-antibody reaction to the profragment region of prorenin;

26) A prorenin activation controlling substance comprising an antibody against the profragment region of prorenin which is capable of inhibiting the prorenin activation in vivo by removal of prorenin based on an antigen-antibody reaction to the profragment region of prorenin antigen-antibody reaction to the profragment region of prorenin;

27) A hypotensor containing at least one of the prorenin activation controlling substances mentioned in any of the above 12) to 26) as an effective ingredient;

28) The hypotensor according to the above 27), wherein about 10% or more hypotensive rate is available as a hypotensive effect at least at the 12th hour after administration in vivo;

29) The hypotensor according to the above 27), wherein a hypotensive effect is selectively achieved only in patients suffering from hypertension;

30) An organ hypertrophy suppressor containing at least one of the prorenin activation controlling substances mentioned in any of the above 12) to 26);

31) The organ hypertrophy suppressor according to the above 30), wherein an organ hypertrophy can be suppressed in heart and/or kidney;

32) An arterial thickening suppressor containing at least one of the prorenin activation controlling substances mentioned in any of the above 12) to 26) as an effective ingredient;

33) A method for a treatment of hypertension using any of the hypotensors mentioned in the above 27) to 29);

34) A method for a treatment of cardiac insufficiency or renal insufficiency using the organ hypertrophy suppressor mentioned in the above 30) or 31); and 35) A method for a treatment of diseases accompanied by thickening of blood vessel using the arterial thickening suppressor mentioned in the above 32).

DETAILED DESCRIPTION OF THE PREFERRED EMBODIMENTS

The present invention will be illustrated in detail as hereunder and the meanings commonly understood by one of ordinary skill in the art to which the present invention pertains, unless otherwise defined. In the present specification, reference is made herein to various methodologies known to those of ordinary skill in the art. Reference documents such as publications setting forth such known methodologies to which reference is made are incorporated herein by reference in their entireties as though set forth in full.

(Effect of Inhibition of Activation of Prorenin In Vivo)

The present inventors have previously found using an anti-human pf antibody that prorenin can be activated to an open-type structure in vitro exhibiting an enzymatic activity without alteration in its primary structure by a specific antibody to an amino acid fragment of pf region of prorenin (Japanese Patent Laid-Open No. H10-279,600; U.S. Pat. No. 5,945,512). On the basis of such a finding, there was prepared an antibody (anti-rat pf antibody) which specifically recognizes a rat pf peptide that is in the same site as the peptide (human pf peptide) of pf region of human prorenin in view of the order of amino acid sequence in the primary structure of rat prorenin and the said antibody was administered to spontaneously hypertensive rats (SHR) which are the pathological animal model for hypertension. As a result, although the said anti-rat pf antibody was able to activate the rat prorenin in vitro without alteration in its primary structure, it showed a continuous hypotensive effect in vivo as shown in Experimental Examples. In general, antibody forms an antigen-antibody complex by combining with an antigen in blood and then the said resulting antigen-antibody complex is removed from the blood by an immune system. Thus, it can be considered that a hypotensive effect is achieved due to removal of prorenin or activated prorenin by combining with an anti-pf antibody. Alternatively, it is conceivable that a hypotensive effect is achieved due to inhibition of combining of prorenin or activated prorenin with its action site as a result of combining of the anti-pf antibody with prorenin or activated prorenin in blood.

In addition, the present inventors synthesized a partial peptide derived from rat prorenin profragment which is an antigen against the above-mentioned anti-rat pf antibody which is able to activate the rat prorenin in vitro and administered it to SHR. Such a peptide is able to competitively inhibit the activation of rat prorenin in vitro by an anti-rat pf antibody like the fact that a human pf peptide inhibits the activation of human prorenin in vitro by an anti-human pf antibody. Thus, such a peptide is able to inhibit the activation of rat prorenin that is resulted by a protein-protein interaction where alteration of the primary structure is not accompanied but that of the higher-order structure is accompanied. When such a peptide was administered to SHR, a sufficient hypotensive effect was achieved at the 12th hour after the administration as will be mentioned later. However, when such a peptide was administered to normal rats, there was no variation in blood pressure. As shown in the Examples which will be mentioned later, the behavior of such a peptide in the course of time was different from that of a renin inhibitor H6137 (manufactured by Sigma) or a neutralized antibody of renin and its hypotensive effect was observed during a long period, so that the hypotensive effect by such a peptide was revealed to be not due to inhibition of renin. In addition, it was also proved that, when such a peptide was continuously administered for 14 days to SHR, hypertrophy of heart and kidney was suppressed and arterial thickening, i.e. blood vessel remodeling, was suppressed as well. Those effects achieved by administration of the above-mentioned peptide are presumed to be achieved by the fact that the said peptide inhibits the activation of rat prorenin with alteration of the structure accompanied by protein-protein interaction in vivo or inhibits rat prorenin or activated rat prorenin to combine with its acting site.

From the above results, it is probable that, in SHR, prorenin exhibits its enzymatic activity by interacting with prorenin-binding protein to activate renin-angiotensin system followed by causing the hypertension and it has been revealed that the pf peptide and anti-pf peptide antibody showed a hypotensive action against hypertension caused by activation of the renin-angiotensin system. Participation of prorenin in hypertension and prorenin activation in vivo by a protein-protein interaction in profragment region of prorenin as such has now been confirmed for the first time. It has been also found that a prorenin activation controlling substance, which is capable of inhibiting the activation of prorenin with alteration in an structure due to protein-protein interaction and the protein-protein interaction of prorenin or activated prorenin with its acting site, is useful as hypotensor, organ hypertrophy suppressor, arterial thickening suppressor, etc.

The number of amino acid residues of the pf peptide of rat prorenin is the same as that of human prorenin pf peptide but the amino acids constituting them are different. In spite of that, as mentioned above, a rat pf peptide, which is in the same site as the human pf peptide in view of the order of amino acid sequence in the primary structure that is an epitope peptide of anti-human pf antibody capable of activating the human prorenin in vitro, and a specific antibody against the said pf peptide showed a hypotensive effect in pathological model rats of hypertension Accordingly, there is no difference among the species in pharmacological action of prorenin participating in hypertension, structural site concerning the activation of prorenin, and mechanism of its activation. Thus, although the hypotensive effect of the above-mentioned peptide was observed in pathological model rats of hypertension, it goes without saying that the same effect can be expected for human hypertension as well by selecting an appropriate peptide in consideration of the amino acid sequence of pf peptide of human prorenin.

Further, as mentioned above, when an inactive enzyme precursor interacts with its specific anti-pf peptide antibody in vitro to express the enzymatic activity or, in other words, protein function, then its mechanism is conserved over the species, so that pf peptide, antibody against the said pf peptide, pathological animal model, and so on are useful as a screening method for selecting the therapeutic medicament for the symptoms caused by expression of the protein function.

(Method for Selecting a Prorenin Activation Controlling Substance)

A method for the selection of a substance that is capable of controlling the activation of prorenin according to the present invention is characterized in using an adjusting ability of the activation of prorenin by the protein-protein interaction in a profragment region of prorenin as an indicator. Here, activation of prorenin by a protein-protein interaction in a profragment region of prorenin means to open an enzymatically active site of prorenin which is not accompanied by the alteration in a primary structure but accompanied by the alteration in a higher-order structure caused by protein-protein interaction in the pf region. Accordingly, although prorenin which is activated by the said protein-protein interaction retains the same amino acid sequence as that of the primary structure of prorenin before being activated, it is able to show a renin-like enzymatic activity. Examples of the protein having a protein-protein interaction in the pf region are antibody which is activated by recognizing the pf peptide, protein which is an action site of prorenin or activated prorenin in vivo, and protein in blood which is capable of activating the prorenin by combining therewith.

The above-mentioned method for selecting a prorenin activation controlling substance can be constructed by utilizing a screening system for pharmaceutical agents that has been known per se. For example, when prorenin and an anti-pf antibody which is capable of activating the prorenin are used to measure the binding of prorenin to the said anti-pf antibody, it is possible to select a substance which inhibits the activation of prorenin. Further, for example, when prorenin and an anti-pf antibody which is capable of activating the prorenin are used to measure the enzymatic activity of the activated prorenin, it is possible to select a substance which inhibits the activation of prorenin or a substance which inhibits the enzymatic activity of prorenin. Needless to say, methods for the selection are not limited thereto. In addition, as mentioned above, the amino acids that constitute the amino acid sequence of pf region of prorenin vary depending upon the species and, therefore, in the selection of a controlling substance for activation of human prorenin, the use of human prorenin and an antibody against pf peptide of the human prorenin is one of the preferred embodiments.

As an example in the concrete, it is possible to construct a screening system utilizing human prorenin and an antibody that is capable of activating the human prorenin by specifically recognizing human prorenin pf peptide prepared according to the description in Japanese Patent Laid-Open No. H10-279,600 and U.S. Pat. No. 5,945,512.

With regard to a substance which is an object to be selected in the above-mentioned selecting method for a prorenin activation controlling substance, candidate substances can be generally utilized as objects for the selection, which are used in a pharmaceutical screening system that has been known per se, such as low-molecular weight compounds, compounds derived from natural substances, peptides, and so on.

Low-molecular weight compounds and peptides that are designed based on amino acid sequence information of pf region of prorenin or, particularly, human prorenin may be used as objects for the selection as well.

Amino acid sequence of pf region of human prorenin has been already known and comprises 43 amino acids (SEQ ID NO: 1 of the Sequence Listing) as shown in Japanese Patent Laid-Open No. 8-285,852. The amino acid sequence of pf peptide of prorenin is useful information for designing a substance which is an object for selecting a prorenin activation controlling substance. Particularly, the information of at least 3 consecutive or, more preferably, at least 4 consecutive amino acid sequences in the amino acid sequence that is from the first to the 19th (pf 1-19), especially from the 5th to the 19th (pf 5-19) and from the 27th to the 41st (pf 27-41) from N-terminal of pf region of prorenin is useful for designing the prorenin activation controlling substance. Amino acid sequences of human-derived pf 1-19, human-derived pf 5-19, human derived pf 27-41, rat-derived pf 1-19, rat-derived pf 5-19 and rat-derived pf 27-41 are shown in SEQ ID NO: 2, NO: 3, NO: 4, NO: 6, NO: 7 and NO: 8, respectively. Hereinafter, a peptide comprising the moieties from the M-th to the N-th ones from N-terminal of pf region will be referred to as "pf M-N".

As mentioned above, in the amino acid sequence of a prorenin pf region, although numbers of the amino acid residues are same even when the species are different, the constituent amino acids are different. In Experimental Examples, the amino acid sequence (SEQ ID NO: 5 of the Sequence Listing) of pf peptide of rat prorenin was exemplified as the information useful for designing the substance that is an object for the selection of prorenin activation controlling substance. In the Examples, fragments of the amino acid sequence of rat prorenin pf region was synthesized, such as pf 1-11 (SEQ ID NO: 9 of Sequence Listing), pf 5-19 (SEQ ID NO: 7 of Sequence Listing), pf 1-4 (SEQ ID NO: 10 of Sequence Listing), pf 1-7 (SEQ ID NO: 11 of Sequence Listing), pf 5-11 (SEQ ID NO: 12 of Sequence Listing), pf 12-19 (SEQ ID NO: 13 of Sequence Listing), pf 11-15 (SEQ ID NO: 14 of Sequence Listing) and pf 27-41 (SEQ ID NO: 8 of Sequence Listing), followed by their hypotensive effect, organ hypertrophy suppressing effect and arterial thickening suppressing effect due to suppression of prorenin activation thereby. However, such sequences are not limited thereto. Anyone ordinary skilled in the art is able to synthesize appropriately at least 3 peptides by a method which is known per se and to design and synthesize a substance, which is able to be an object to be selected, based on the peptide synthesized as such.

Further, as mentioned above, a specific antibody to rat pf peptide that is in the same site in view of the order of amino acid sequence in the primary structure as the human pf peptide which is an epitope of an anti-human pf antibody which is able to activate human prorenin in vitro showed a hypotensive action in a hypertensive pathological model rats and, therefore, it is easily presumed that the human prorenin pf peptide where the amino acid sequence order in the primary structure is same as the rat pf peptide shows the similar effect to human being as well. As one of the preferred embodiments, the pf peptide of human prorenin is used as the information for designing a substance that is to be an object for the selection.

The substance which is to be an object for the selection, when it is a peptide, is able to be appropriately designed on the basis of information of amino acid sequence in the prorenin pf region as mentioned above and provided for the selection. The amino acid consisting the said peptide are not always necessary to be same as the amino acid sequence of the prorenin region but that may be a peptide where mutation such as deficiency, substitution, addition and insertion may be introduced into the amino acid sequence of the said peptide so far as the same function as the said peptide is available (hereinafter, that may sometimes be called "equivalent peptide").

The substance that is to be an object for the selection may also be a low-molecular weight compound that is obtained by drug design based on structural complementarity according to the information on the basis of the secondary and/or tertiary structure of amino acid sequence of pf region.

As a result of the above-mentioned method, a substance is obtained which is able to inhibit the activation of human prorenin by anti-human pf peptide antibody. From the substances obtained, it is also possible to select the substances having hypotensive effect, organ hypertrophy suppressing effect and arterial thickening suppressing effect, by accumulating the information based on peptide having a partial sequence selected from the amino acid sequence of pf region, known hypotensors, and the like or carrying out an experiments using an animal model and so on.

(A Prorenin Activation Controlling Substance)

Thus, the present invention further provides a prorenin activation controlling substance that is capable of controlling the activation of prorenin due to the protein-protein interaction in the pf region of prorenin.

One of the embodiments of the present invention is a prorenin activation controlling substance that is capable of controlling the activation of human prorenin.

The prorenin activation controlling substance according to the present invention may be a substance which competitively inhibits the protein-protein interaction that leads to prorenin activation, a substance which antagonistically inhibits the binding of prorenin or activated prorenin at the site on which they act, a substance which has antigen-antibody reactivity to prorenin or activated prorenin, a substance which acts on the site on which prorenin or activated prorenin act to inhibit the action of prorenin or activated prorenin, and the like.

One of the preferred embodiments is that the above-mentioned prorenin activation controlling substance is the one that has a function of inhibiting the prorenin activation based on the protein-protein interaction in the pf region of prorenin and has no renin-inhibiting activity. Thus, the above-mentioned prorenin activation controlling substance has no direct inhibiting action on renin as its action mechanism. Therefore, unlike renin inhibitors, it is able to inhibit the activity of prorenin that is activated in a pathological state without inhibiting a renin-angiotensin system that has an important role in the homeostatic mechanism of life. That is an important characteristic of the prorenin activation controlling substance according to the present invention.

In the concrete, a peptide having a partial sequence selected from the amino acid sequence of pf region of prorenin, an equivalent peptide to the said peptide, a low-molecular weight substance designed from the information of the amino acid sequence of pf region of prorenin, an antibody against the pf region of prorenin, and so on are exemplified, although they are not limited thereto.

One of the preferred embodiments is that the above-mentioned peptide is a peptide having a partial sequence selected from the amino acid sequence of pf region of human prorenin or an equivalent peptide thereto. For example, with regard to a peptide derived from the amino acid sequence of pf region of human prorenin, the following peptides may be exemplified.

hp 1: human prorenin pf 1-11 (SEQ ID NO: 15 of the Sequence Listing)

hp 2: human prorenin pf 5-11 (SEQ ID NO: 16 of the Sequence Listing)

hp 3: human prorenin pf 5-19 (SEQ ID NO: 3 of the Sequence Listing)

hp 4: human prorenin pf 1-4 (SEQ ID NO: 17 of the Sequence Listing)

hp 5: human prorenin pf 1-7 (SEQ ID NO: 18 of the Sequence Listing)

hp 6: human prorenin pf 12-19 (SEQ ID NO: 19 of the Sequence Listing)

hp 7: human prorenin pf 11-15 (SEQ ID NO: 20 of the Sequence Listing) and hp 8: human prorenin pf 27-41 (SEQ ID NO: 4 of the Sequence Listing)

In controlling the activation of prorenin, one of those peptides may be used or two or more thereof may be mixed to use.

As one of the preferred embodiments, the above-mentioned antibody is an antibody against the human prorenin pf region. For example, anti-human pf antibodies maybe exemplified, which are obtained by using the following peptides derived from the amino acid sequence of human prorenin pf region as antigens.

hp 9: human prorenin pf 1-15 (SEQ ID NO: 21 of the Sequence Listing)

hp 10: human prorenin pf 18-30 (SEQ ID NO: 22 of the Sequence Listing) and hp 11: human prorenin pf 30-41 (SEQ ID NO: 23 of the Sequence Listing)

In controlling the activation of prorenin, only one kind of antibody may be used or two or more kinds thereof may be mixed to use. When the above-mentioned antibody is used in pharmaceuticals as a prorenin activation controlling substance, the said antibody is preferred to be a monoclonal antibody that can be obtained by a known method and is also preferred to be prepared as a human type antibody. As to a method for the preparation of human type antibody, it is possible to utilize a method known per se (*J. Immunol. Methods*, 100, 5-40, 1987).

(Hypotensors)

As one of the embodiments, the present invention provides a hypotensor containing at least one kind of the above-mentioned prorenin activation controlling substances as an effective ingredient. The said hypotensor is characterized in that, at even 12 hours later from its administration into living body, it still achieves a sufficient hypotensive action and the duration of the effect is quite long. For example, in an experiment in pathological model rats of hypertension, a hypotensive rate of at least around 10% as SBP (systolic blood pressure) values (%) was shown after 12 hours from the administration. Although that value is not so high as hypotensors, one of ordinary skill in the art is easily able to give higher effect by improving dose, administration period and/or administering method, and so on. On the other hand, the in vivo effect of renin inhibitors, which are the hypotensors being available hitherto, appears immediately after the administration and, after that, it disappears within minutes. Further, the in vivo effect of ACE inhibitors continues for 6~8 hours after the administration, though it disappears after that. Consequently, the sustained hypotensive effect of the hypotensors according to the present invention for long time is a very useful characteristic when improvement of hypertension is taken into consideration.

Further, the hypotensors according to the present invention shows a hypotensive effect by a mechanism which is different from that of remedies for hypertension that have been available hitherto such as ACE inhibitors and renin inhibitors and they may be used in a treatment of hypertension together with the remedies for hypertension and the like that have been already available.

Furthermore, the above-mentioned hypotensors are able to achieve their hypotensive effect selectively only to the patients suffering from hypertension. In the experiment comparing normal rats with pathological model rats of hypertension, it was proved that the above-mentioned hypotensors acted on pathological model rats of hypertension only. Thus, the hypotensor according to the present invention is useful for the treatment of hypertension.

(Organ Hypertrophy Suppressors)

The present invention further provides a novel suppressor for hypertrophy of organs containing at least one kind of the above-mentioned prorenin activation controlling substances as an effective ingredient. The organ hypertrophy suppressor according to the present invention is able to suppress the organ hypertrophy in heart and/or kidney. Accordingly, the said organ hypertrophy suppressor can be expected to have an effect in cardiac insufficiency and renal insufficiency.

(Arterial Thickening Suppressors)

The present invention provides a novel suppressor for thickening of artery containing at least one kind of the above-mentioned prorenin activation suppressing substances as an effective ingredient. The arterial thickening suppressor according to the present invention is able to suppress the thickening, that is to say remodeling of blood vessel, of pulmonary artery, femoral artery, and so on. Accordingly, the said arterial thickening suppressor is effective for the diseases accompanied by thickening of blood vessel that is to say remodeling of blood vessel, such as arteriosclerosis.

(Making into Pharmaceutical Preparations)

In making the above-mentioned hypotensors, organ hypertrophy suppressors and arterial thickening suppressors into pharmaceutical preparations, known methods may be appropriately used depending upon the physical property of the peptide or the low-molecular weight compound. For example, methods for manufacturing tablets, capsules, aqueous solution preparations, ethanolic solution preparations, liposome preparations, fatty emulsions, inclusion compounds including cyclodextrin or the like, and so on, may be utilized.

Powder, pills, capsules and tablets may be manufactured using excipient such as lactose, glucose, sucrose and mannitol; disintegrating agent such as starch and sodium alginate; lubricant such as magnesium stearate and talc; binder such as polyvinyl alcohol, hydroxypropyl cellulose and gelatin; surface-active agent such as fatty acid ester; plasticizer such as glycerol; etc. In the manufacture of tablets and capsules, a solid pharmaceutical carrier is used.

Suspension may be manufactured by using water; saccharide such as sucrose, sorbitol and fructose; glycols such as PEG; and oils.

Solutions for injection can be prepared using a carrier comprising a salt solution, a glucose solution or a mixture of salt water and a glucose solution.

Manufacture of liposome preparation may be for example carried out in such a manner that a solution where the said substance is dissolved in a solvent (such as ethanol) is added to a solution where phospholipid is dissolved in an organic solvent (such as chloroform), and the solvents are evaporated therefrom, and then a phosphate buffer is added thereto followed by subjecting to shaking, ultrasonic treatment and centrifugal separation and the supernatant is filtered to recover.

Manufacture of a fatty emulsion may be for example carried out in such a manner that the said substance, oil component (such as soybean oil, sesame oil, olive oil and vegetable oil, MCT, and the like), emulsifier (such as phospholipid), etc. are mixed and heated and a necessary amount of water is added to the resulting solution followed by subjecting to emulsifying/homogenizing treatment using an emulsifier (homogenizer such as that of a high-pressure type, a ultrasonic type, etc.). It is also possible that the product is freeze-dried. In the manufacture of a fatty emulsion, an emulsifying aid may be used and glycerol and saccharides (such as glucose, sorbitol, fructose and the like) are exemplified as the emulsifying aid.

Manufacture of an inclusion compound with cyclodextrin may be carried out for example in such a manner that a solution where cyclodextrin is dissolved in water or the like by heating is added to a solution where the said substance is dissolved in a solvent (such as ethanol), and the mixture is cooled to separate precipitate followed by filtering and drying with sterilization. With regard to the cyclodextrin used there, cyclodextrin having different pore diameters ($\alpha$, $\beta$ and $\gamma$ types) may be appropriately selected depending upon the size of the said substance.

Dose of the above-mentioned hypotensor, organ hypertrophy suppressor or arterial thickening suppressor may be appropriately selected depending upon symptom, sex, age and body weight of the patient. Route for the administration may be either of oral and parenteral. One of the preferred embodiments is that an orally applicable preparation is manufactured and is administered per os. An examples of the dose is around 1~1,000 µg per day.

EXAMPLES

The present invention will now be more specifically illustrated by way of the following examples although the present invention is not limited thereto but can be variously modified within a range of not departing from the technical idea of the present invention.

Example 1

(Preparation of Antibody Recognizing a Peptide Derived from pf Region of Rat Prorenin)

Pf 1-15 (SEQ ID NO: 24 of the Sequence Listing), pf 18-30 (SEQ ID NO: 25 of the Sequence Listing) and pf 30-41 (SEQ ID NO: 26 of the Sequence Listing), which are pf peptides of rat prorenin, were prepared by a solid phase method in a conventional manner and, using those oligopeptides as antigens, antibodies against them—Ab 1, Ab 2 and Ab 3—were prepared according to the descriptions of Examples of Japanese Patent Laid-Open No. H10-279,600 and U.S. Pat. No. 5,945,512. To be more specific, the above-mentioned oligopeptide which was an antigen was immunized to rabbit of a New Zealand white species together with an adjuvant to prepare anti-serum. The resulting anti-serum was purified according to the method mentioned in the patents.

Ab 1: antibody which specifically recognizes pf 1-15

Ab 2: antibody which specifically recognizes pf 18-30

Ab 3: antibody which specifically recognizes pf 30-41

Further, equal amounts of those antibodies were mixed to prepare Ab mix. Furthermore, activation of prorenin by those antibodies in vitro was investigated by the methods mentioned in the patents and it was confirmed that those antibodies were able to activate prorenin.

Example 2

(Preparation of Peptide Derived from pf Region of Rat Prorenin)

The following peptides derived from the sequence of pf region of rat prorenin were synthesized by a solid phase method in a conventional manner.

p 1: pf 1-11 (SEQ ID NO: 9 of the Sequence Listing)
p 2: pf 5-19 (SEQ ID NO: 7 of the Sequence Listing)
p 3: pf 27-41 (SEQ ID NO: 8 of the Sequence Listing)
p 1a: pf 1-4 (SEQ ID NO: 10 of the Sequence Listing)
p 1b: pf 1-7 (SEQ ID NO: 11 of the Sequence Listing)
p 1c: pf 5-11 (SEQ ID NO: 12 of the Sequence Listing)
p 2a: pf 12-19 (SEQ ID NO: 13 of the Sequence Listing) and
p 2b: pf 11-15 (SEQ ID NO: 14 of the Sequence Listing)

Further, equal amounts of p 1, p 2 and p 3 were mixed to prepare a P mix.

Experimental Example 1

(Investigation of Hypotensive Effect by Anti-pf Peptide Antibody and pf Peptide)

A group comprising three SHR male rats (12~14 weeks age; body weight: 258~310 g) that are pathological model animals of hypertension was used. Ab mix prepared in Example 1, P mix prepared in Example 2 and dissolved in a physiological saline, and anti-renin neutralizing antibody and captopril, which were the drugs used for comparative study, were intravenously administered at the dose of 0.44 mg/kg, 0.6 mg/kg, 0.12 mg/kg and 100 mg/kg, respectively. Measurement of blood pressure was carried out in such a manner that a cannula inserted into common carotid artery and external carotid artery was connected to a pressure transducer (P23XL; Gould Electronics) and introduced into a pressure processor signal conditioner (Gould Electronics), followed by carrying out measurement every ten minutes until 1 hour from administration of the test substance and every one hour thereafter and the data were recorded on a thermal array recorder (RS 3400; Gould Electronics).

The anti-renin neutralizing antibody that was a drug for comparative study did not show any hypotension until 6 hours from the administration and, at the 6th hour and the 24th hour, tendencies of hypotension of 11% and 14%, respectively, were noted. P mix and Ab mix showed continuous hypotension of 9% at the highest and 7% at the highest, respectively after administration until the completion of the experiment. In the case of captopril that was a positive control, the maximum hypotension (31% at the highest) was achieved until the 6th hour from the administration and, at the completion of the experiment at the 24th hour, no hypotensive action was noted.

As a result, it was revealed that P mix and Ab mix showed a hypotensive effect with a different course of time as comparing to anti-renin neutralizing antibody and captopril which was an ACE inhibitor. Thus, it was found that P mix and Ab mix showed a sustaining hypotensive ability for a very long period immediately after the administration. In addition, it was presumed therefrom that the hypotensive effect of P mix and Ab mix was not due to inhibition of renin activity.

Experimental Example 2

On the basis of the data obtained in Experimental Example 1, a test was carried out for P mix with an increased dose (2 mg/kg) using five cases of SHR in the same manner as in Experimental Example 1. A physiological saline was used for a control group. As a result, a transient hypotensive action of 11% was noted immediately after administration. Although that recovered after 5 minutes from administration, hypotension gradually took place again thereafter to an extent of 9% at the highest whereupon a significant difference was noted as compared with the control group after 1~6 hour(s) from administration. Thus, it was confirmed that P mix had a biphasic hypotensive action.

Experimental Example 3

A test was carried out for p 1 (pf 1-11), p 2 (pf 5-19) and p 3 (pf 27-41) prepared in Example 2 in the same manner as in Experimental Example 1 using 2 or 4 cases of SHR. The result was that, in the case of administration of 2 mg/kg of p 1, a transient hypertensive action of around 6% was noted immediately after administration, that recovered after 5 minutes from administration, then a hypotensive gradually took place thereafter to an extent of 6% at the highest and a sustained effect was confirmed until 24th hour. In the case of administration of 10 mg/kg, hypotension of about 7% was noted at 6 hours after administration and, until 24th hour, a sustained effect to an extent of around 10% at the highest was noted. In the case of administration of 2 mg/kg of p 2, a transient hypotension of around 35% was noted immediately after administration, it recovered at 5 minutes after administration and, after that, a sustained hypotensive action was confirmed until 24th hour to an extent of around 6% at the highest. In the case of administration of 2 mg/kg of p 3, a transient hypertension of around 14% was noted immediately after administration, that recovered at 5 minutes after administration and no action was confirmed thereafter. In the case of administration of 10 mg/kg, a hypotension of 7% was noted after 2 hours and, until 24th hour, a sustained hypotensive action where 11% was the highest was confirmed.

Thus, it was found that a peptide comprising an amino acid sequence of from the first to the 11th or from the 5th to the 19th from N-terminal of pf region of rat prorenin and a peptide comprising an amino acid sequence of from the 27th to the 41st corresponding to the C-terminal side of pf region of rat prorenin had a sustained hypotensive action.

Such a result also shows that the transient hypotension immediately after administration of P mix is an action of p 2 and the sustained hypotensive action thereafter is an interactional action of p 1, p 2 and p3.

Experimental Example 4

As a comparative experiment, the same test as in Example 2 was carried out using five rats having normal blood pressure (WKY rats) of the same weeks age in place of SHR. Except a transient hypotension immediately after the administration, P mix did not show any hypotension at all. Accordingly, it was confirmed that P mix did not show a sustained hypotensive action in normal rats.

Experimental Example 5

The same test as in Experimental Example 1 was carried out for each 2 cases of SHR using p 1 (pf 1-11), p 1a (pf 1-4), p 1b (pf 1-7), p 1c (pf 5-11), p 2a (pf 12-19) and p 2b (pf 11-15) prepared in Example 2 at the dose of 1 mg/kg for p 2a (pf 12-19) and p 2b (pf 11-15) and 10 mg/kg for all other peptides.

In result, p 1 showed a sustained hypotension to an extent of 14% at the highest until 24 hours after administration. Although p 1a showed a transient hypertension of 13% immediately after administration, it showed a sustained hypotension of 13% at the highest until 24 hours thereafter. Although p 1b showed a transient hypertension of 17% immediately after administration, it showed a sustained hypotension of 13% at the highest until 24 hours thereafter. Although p 1c showed a transient hypertension of 21% immediately after administration, it showed a sustained hypotension of 16% at the highest until 24 hours thereafter. Although p 2a showed a transient hypertension of 6% immediately after administration, it showed a sustained hypotension of 14% at the highest until 24 hours thereafter. The same effect was achieved by the use of p 2b as well.

As a result, it was found that a peptide derived from an amino acid sequence of from the first to the 19th from N-terminal of the amino acid sequence of pf region of rat prorenin had a sustained hypotensive action Experimental Example 6

Each of p 2a (pf 12-19) prepared in Example 2 and H 6137 (which is a renin inhibitor; D-His-Pro-Phe-His-Leu-$\psi$-[$CH_2NH$]-Leu-Val-Tyr; Sigma) was used and administered at the dose of 1 mg/kg via a cannula from external carotid artery and the changes of blood pressure in a course of time were measured by the method mentioned in Example 1.

The result was that p 2a showed a sustained hypotension of 11% at the highest at 5~8 hours after administration and that effect continued at least for 12 hours from the administration. On the other hand, although H 6137 showed a sustained hypotension of 9% at the highest at 3~8 hours after administration, a tendency of disappearance of the effect was observes after 6 hours of the administration and thereafter.

It has been made clear that, although p 2a requires long time until its action appears, its action is long lasting, and in the case of H 6137, time until appearance of the action is quick but its acting period is short. From the difference in the behaviors of the hypotensive effect in a course of time as such, it is presumed that the hypotensive effect of prorenin activation controlling substance represented by p 2a is not due to inhibition of renin.

Experimental Example 7

The p 1c (pf 5-11) prepared in Example 2 was intravenously administered once daily for consecutive 14 days at the dose of 1.6 mg/kg to a group comprising 4 SHRs. On the 14th day, the rats were killed by bleeding, followed by excising heart and kidney to measure their weights. The result is shown in Table 1 in terms of weight of the organ per 100 g of body weight. As shown in Table 1, the weight of heart and kidney of SHR to which p 1c was administered was light as compared with a control group to which a physiological saline was administered whereby it is apparent that p 1c suppresses hypertrophy of heart and kidney.

TABLE 1

| | | Weight of Organ (g/g body weight) | | |
|---|---|---|---|---|
| Substance Administered | | Heart | Right Kidney | Left Kidney |
| Physiological saline | 1 | 0.43 | 0.38 | 0.40 |
| | 2 | 0.47 | 0.39 | 0.44 |
| | Mean Value | 0.45 | 0.39 | 0.42 |
| | Standard Error | 0.02 | 0.00 | 0.02 |
| p 1c | 3 | 0.37 | 0.34 | 0.34 |
| | 4 | 0.40 | 0.35 | 0.35 |
| | 5 | 0.39 | 0.35 | 0.35 |
| | 6 | 0.40 | 0.33 | 0.35 |
| | Mean Value | 0.39 | 0.34 | 0.35 |
| | Standard Error | 0.01 | 0.00 | 0.00 |

Experimental Example 8

Pulmonary, superior mesenteric artery and femoral artery were excised from the rats tested in Experimental Example 7 and their weights were measured. Weight of each artery was calculated in terms of weight per each area, followed by further converting the calculated value into the value per body weight of each rat and the results were compared and shown in Table 2. As shown in Table 2, weight of each artery in the SHR to which p 1c was administered was apparently light as compared with that of the control group whereupon it has been found that p 1c suppresses the thickening of artery, i.e. remodeling of blood vessel.

TABLE 2

| | | Weight of Artery ($mg/mm^2$/g body weight) | | |
|---|---|---|---|---|
| Substance Administered | | Pulmonary Artery | Superior Mesenteric Artery | Femoral Artery |
| Physiological saline | 1 | 0.00093 | 0.00084 | 0.00138 |
| | 2 | 0.00119 | 0.00107 | 0.00135 |
| | Mean Value | 0.00106 | 0.00096 | 0.00137 |
| | Standard Error | 0.00013 | 0.00012 | 0.00002 |
| p 1c | 3 | 0.00067 | 0.00094 | 0.00068 |
| | 4 | 0.00087 | 0.00095 | 0.00094 |
| | 5 | 0.00088 | 0.00096 | 0.00106 |
| | 6 | 0.00082 | 0.00100 | 0.00087 |
| | Mean Value | 0.00081 | 0.00096 | 0.00089 |
| | Standard Error | 0.00005 | 0.00001 | 0.00008 |

Example 3

A screening system was constructed using human prorenin prepared according to the description in Japanese Patent Laid-Open No. H10-279,600 and U.S. Pat. No. 5,945,512 and an antibody which is able to activate human prorenin by specifically recognizing the human prorenin pf peptide. A test was carried out using a screening system that was constructed for candidate compounds to confirm their action to the activation of human prorenin by the anti-pf peptide antibody. By such a method, substances can be obtained which are capable of inhibiting the activation of human prorenin by anti-human pf peptide antibody. In addition, information that is accumulated on the basis of peptides selected from human prorenin profragment region, known hypotensors, and the like and also the result of the experiments using the animal model can make it possible to select substances having hypotensive effect, organ hypertrophy suppressing effect and artery thickening suppressing effect from the resulting substances.

POSSIBILITY OF INDUSTRIAL USAGE

The present invention provides a method for the selection of a substance which is capable of controlling the activation of prorenin where adjusting ability for activation of prorenin by protein-protein interaction in a profragment region of prorenin is used as an indicator and also provides a prorenin activation controlling substance having a function of controlling the activation of prorenin based on protein-protein interaction by a profragment region of prorenin. In addition, by the use of the above-mentioned prorenin activation controlling substance, it is possible to further provide hypotensor, organ hypertrophy suppressor and arterial thickening suppressor having a novel mechanism. When such a pharmaceutical agent is used either solely or together with the already-known pharmaceutical agent, it can be effectively utilized for the treatment of hypertension, cardiac insufficiency, renal insufficiency, arteriosclerosis, the diseases accompanied by blood vessel remodeling and so on.

What is claimed is:

1. A prorenin activation controlling substance consisting of the amino acid sequence selected from the group consisting of SEQ ID NO: 7 to SEQ ID NO: 14.

2. A prorenin activation controlling substance consisting of the amino acid sequence selected from the group consisting of SEQ ID NOs: 3, 4, and 7-20.

3. A hypotensor comprising the prorenin activation controlling substance of claim 1 as an effective ingredient.

4. An organ hypertrophy suppressor comprising the prorenin activation controlling substance of claim 1 as an effective ingredient.

5. An arterial thickening suppressor comprising the prorenin activation controlling substance of claim 1 as an effective ingredient.

* * * * *

```
                         SEQUENCE LISTING

<160> NUMBER OF SEQ ID NOS: 26

<210> SEQ ID NO 1
<211> LENGTH: 43
<212> TYPE: PRT
<213> ORGANISM: Homo sapiens

<400> SEQUENCE: 1

Leu Pro Thr Asp Thr Thr Thr Phe Lys Arg Ile Phe Leu Lys Arg Met
 1               5                  10                  15

Pro Ser Ile Arg Glu Ser Leu Lys Glu Arg Gly Val Asp Met Ala Arg
            20                  25                  30

Leu Gly Pro Glu Trp Ser Gln Pro Met Lys Arg
        35                  40

<210> SEQ ID NO 2
<211> LENGTH: 19
<212> TYPE: PRT
<213> ORGANISM: Homo sapiens

<400> SEQUENCE: 2

Leu Pro Thr Asp Thr Thr Thr Phe Lys Arg Ile Phe Leu Lys Arg Met
 1               5                  10                  15

Pro Ser Ile

<210> SEQ ID NO 3
<211> LENGTH: 15
<212> TYPE: PRT
<213> ORGANISM: Homo sapiens

<400> SEQUENCE: 3

Thr Thr Thr Phe Lys Arg Ile Phe Leu Lys Arg Met Pro Ser Ile
 1               5                  10                  15

<210> SEQ ID NO 4
<211> LENGTH: 15
<212> TYPE: PRT
<213> ORGANISM: Homo sapiens

<400> SEQUENCE: 4

Gly Val Asp Met Ala Arg Leu Gly Pro Glu Trp Ser Gln Pro Met
 1               5                  10                  15

<210> SEQ ID NO 5
<211> LENGTH: 43
<212> TYPE: PRT
<213> ORGANISM: Rattus norvegicus
```

```
<400> SEQUENCE: 5

Leu Pro Thr Asp Thr Ala Ser Phe Gly Arg Ile Leu Leu Lys Lys Met
 1               5                  10                  15

Pro Ser Val Arg Glu Ile Leu Glu Arg Gly Val Asp Met Thr Arg
            20                  25                  30

Ile Ser Ala Glu Trp Gly Glu Phe Ile Lys Lys
        35                  40

<210> SEQ ID NO 6
<211> LENGTH: 19
<212> TYPE: PRT
<213> ORGANISM: Rattus norvegicus

<400> SEQUENCE: 6

Leu Pro Thr Asp Thr Ala Ser Phe Gly Arg Ile Leu Leu Lys Lys Met
 1               5                  10                  15

Pro Ser Val

<210> SEQ ID NO 7
<211> LENGTH: 15
<212> TYPE: PRT
<213> ORGANISM: Rattus norvegicus

<400> SEQUENCE: 7

Thr Ala Ser Phe Gly Arg Ile Leu Leu Lys Lys Met Pro Ser Val
 1               5                  10                  15

<210> SEQ ID NO 8
<211> LENGTH: 15
<212> TYPE: PRT
<213> ORGANISM: Rattus norvegicus

<400> SEQUENCE: 8

Gly Val Asp Met Thr Arg Ile Ser Ala Glu Trp Gly Glu Phe Ile
 1               5                  10                  15

<210> SEQ ID NO 9
<211> LENGTH: 11
<212> TYPE: PRT
<213> ORGANISM: Rattus norvegicus

<400> SEQUENCE: 9

Leu Pro Thr Asp Thr Ala Ser Phe Gly Arg Ile
 1               5                  10

<210> SEQ ID NO 10
<211> LENGTH: 4
<212> TYPE: PRT
<213> ORGANISM: Rattus norvegicus

<400> SEQUENCE: 10

Leu Pro Thr Asp
 1

<210> SEQ ID NO 11
<211> LENGTH: 7
<212> TYPE: PRT
<213> ORGANISM: Rattus norvegicus

<400> SEQUENCE: 11

Leu Pro Thr Asp Thr Ala Ser
 1               5
```

```
<210> SEQ ID NO 12
<211> LENGTH: 7
<212> TYPE: PRT
<213> ORGANISM: Rattus norvegicus

<400> SEQUENCE: 12

Thr Ala Ser Phe Gly Arg Ile
 1               5

<210> SEQ ID NO 13
<211> LENGTH: 8
<212> TYPE: PRT
<213> ORGANISM: Rattus norvegicus

<400> SEQUENCE: 13

Leu Leu Lys Lys Met Pro Ser Val
 1               5

<210> SEQ ID NO 14
<211> LENGTH: 5
<212> TYPE: PRT
<213> ORGANISM: Rattus norvegicus

<400> SEQUENCE: 14

Ile Leu Leu Lys Lys
 1               5

<210> SEQ ID NO 15
<211> LENGTH: 11
<212> TYPE: PRT
<213> ORGANISM: Homo sapiens

<400> SEQUENCE: 15

Leu Pro Thr Asp Thr Thr Thr Phe Lys Arg Ile
 1               5                  10

<210> SEQ ID NO 16
<211> LENGTH: 7
<212> TYPE: PRT
<213> ORGANISM: Homo sapiens

<400> SEQUENCE: 16

Thr Thr Thr Phe Lys Arg Ile
 1               5

<210> SEQ ID NO 17
<211> LENGTH: 4
<212> TYPE: PRT
<213> ORGANISM: Homo sapiens

<400> SEQUENCE: 17

Leu Pro Thr Asp
 1

<210> SEQ ID NO 18
<211> LENGTH: 7
<212> TYPE: PRT
<213> ORGANISM: Homo sapiens

<400> SEQUENCE: 18

Leu Pro Thr Asp Thr Thr Thr
 1               5
```

-continued

```
<210> SEQ ID NO 19
<211> LENGTH: 8
<212> TYPE: PRT
<213> ORGANISM: Homo sapiens

<400> SEQUENCE: 19

Phe Leu Lys Arg Met Pro Ser Ile
 1               5

<210> SEQ ID NO 20
<211> LENGTH: 5
<212> TYPE: PRT
<213> ORGANISM: Homo sapiens

<400> SEQUENCE: 20

Ile Phe Leu Lys Arg
 1               5

<210> SEQ ID NO 21
<211> LENGTH: 15
<212> TYPE: PRT
<213> ORGANISM: Homo sapiens

<400> SEQUENCE: 21

Leu Pro Thr Asp Thr Thr Thr Phe Lys Arg Ile Phe Leu Lys Arg
 1               5                  10                  15

<210> SEQ ID NO 22
<211> LENGTH: 13
<212> TYPE: PRT
<213> ORGANISM: Homo sapiens

<400> SEQUENCE: 22

Ser Ile Arg Glu Ser Leu Lys Glu Arg Gly Val Asp Met
 1               5                  10

<210> SEQ ID NO 23
<211> LENGTH: 12
<212> TYPE: PRT
<213> ORGANISM: Homo sapiens

<400> SEQUENCE: 23

Met Ala Arg Leu Gly Pro Glu Trp Ser Gln Pro Met
 1               5                  10

<210> SEQ ID NO 24
<211> LENGTH: 15
<212> TYPE: PRT
<213> ORGANISM: Rattus norvegicus

<400> SEQUENCE: 24

Leu Pro Thr Asp Thr Ala Ser Phe Gly Arg Ile Leu Leu Lys Lys
 1               5                  10                  15

<210> SEQ ID NO 25
<211> LENGTH: 13
<212> TYPE: PRT
<213> ORGANISM: Rattus norvegicus

<400> SEQUENCE: 25

Ser Val Arg Glu Ile Leu Glu Glu Arg Gly Val Asp Met
 1               5                  10
```

```
<210> SEQ ID NO 26
<211> LENGTH: 12
<212> TYPE: PRT
<213> ORGANISM: Rattus norvegicus

<400> SEQUENCE: 26

Met Thr Arg Ile Ser Ala Glu Trp Gly Glu Phe Ile
 1               5                  10
```